United States Patent [19]

Regnat

[11] Patent Number: 5,648,547

[45] Date of Patent: Jul. 15, 1997

[54] BIS-PHOSPHEPINES AND PROCESSSES FOR THEIR PREPARATION

[75] Inventor: Dieter Regnat, Eppstein, Germany

[73] Assignee: Hoechst AG, Frankfurt, Germany

[21] Appl. No.: 531,470

[22] Filed: Sep. 21, 1995

[30] Foreign Application Priority Data

Sep. 23, 1994 [DE] Germany ............ 44 33 952.6

[51] Int. Cl.[6] .................................. C07F 9/02
[52] U.S. Cl. .................................. 568/12
[58] Field of Search .................................. 568/12

[56] References Cited

U.S. PATENT DOCUMENTS 5,332,846  7/1994  Devon et al. ............ 568/12

OTHER PUBLICATIONS

Chemical Abstracts, vol. 78, No. 17, 1973, Columbus Ohio, US; abstract No. 111450b.

*Primary Examiner*—Joseph Conrad
*Attorney, Agent, or Firm*—Connolly & Hutz

[57] ABSTRACT

The invention relates to bis-phosphepines of the formula (I):

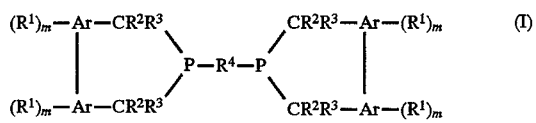

where:

Ar—Ar is biphenyl, 1,1'-binaphthyl or 1-phenylnaphthyl, $R^1$ independently of one another are F, $(C_1-C_8)$-alkyl or $(C_1-C_8)$-alkoxy, m is 0, 1, 2, 3 or 4, $R^2$ and $R^3$ independently of one another are H, $(C_1-C_{20})$-alkyl, $(C_6-C_{20})$-aryl, $(C_7-C_{20})$-aralkyl, $(C_7-C_{20})$-alkaryl or $(C_3-C_{20})$-cycloalkyl and $R^4$ is $(C_1-C_{10})$-alkylene, it also being possible for the alkylene chain to contain oxygen atoms and N-alkyl groups, $(C_3-C_{10})$-cycloalkylene, $(C_8-C_{22})$-arylene-bisalkyl or $(C_6-C_{10})$-arylene, the group $CR^2R^3$ always being adjacent to the Ar—Ar bond.

The invention further relates to processes for the preparation of compounds of the formula (I).

6 Claims, No Drawings

BIS-PHOSPHEPINES AND PROCESSSES FOR THEIR PREPARATION

The present invention relates to bis-phosphepines, i.e. bidentate phosphine ligands, and to processes for their preparation.

Compounds containing two phosphino groups in the molecule (bidentate phosphine ligands) play an important part in a number of processes in which a transition metal complex is used as a catalyst. See also A. Miyashita et al. in Tetrahedron Lett. 34, (1993), 2351 and in J. Am. Chem. Soc. 102, (1980), 7932; R. Noyori et al., Tetrahedron 40, (1984), 1245; H. Takaya, Tetrahedron Lett. 34, (1993), 1615. Hydrogenation, hydroformylation and carbonylation reactions or the alkylation and arylation of aromatics may be mentioned as examples of such processes.

Considering the multitude of possible uses of bidentate phosphine ligands, there is a need for novel phosphine ligands in order on the one hand to complement and expand their range of possible uses, and on the other hand to be able to perform certain reactions in a particularly favorable manner.

This object is achieved by bis-phosphepines of the formula (I):

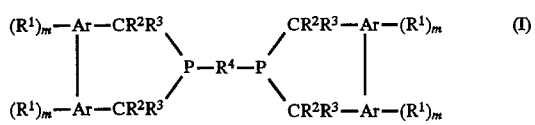

where:

Ar—Ar is biphenyl, 1,1'-binaphthyl or 1-phenylnaphthyl, $R^1$ independently of one another are F, ($C_1$–$C_8$)-alkyl or ($C_1$–$C_8$)-alkoxy, m is 0, 1, 2, 3 or 4, $R^2$ and $R^3$ independently of one another are H, ($C_1$–$C_{20}$)-alkyl, ($C_6$–$C_{20}$)-aryl, ($C_7$–$C_{20}$)-aralkyl, ($C_7$–$C_{20}$)-alkaryl or ($C_3$–$C_{20}$)-cycloalkyl and $R^4$ is ($C_1$–$C_{10}$)-alkylene, it also being possible for the alkylene chain to contain oxygen atoms and N-alkyl groups, ($C_3$–$C_{10}$)-cycloalkylene, ($C_8$–$C_{22}$)-arylenebisalkyl or ($C_6$–$C_{10}$)-arylene, the group $CR^2R^3$ always being adjacent to the Ar—Ar bond.

The methylene radical, the ethylene radical, the n-propylene radical, the n-butylene radical, the 2,2'-bis-methylene-1,1'-biphenyl radical, the 2,2'-bis-methylene-1,1'-binaphthyl radical and the various phenylene, xylylene, biphenylene, binaphthylene and naphthylene radicals may be mentioned specifically for $R^4$.

The phosphorus compounds of the formula (I) can be in either the (R,R), (R,S) or (S,S) form or else in the (RS) form.

Compounds of the formula (I) where m is equal to zero and $R^2$ and $R^3$ are H are of particular interest.

The following compounds may be mentioned specifically:

4,5,4',5'-tetrahydro-3H,3'H-4,4'-butane-1,4-diyl-bis-dinaphtho[2,1-c:1',2'-e]phosphepine 4,5,4',5'-tetrahydro-3H,3'H-4,4'-methanediyl-bis-dinaphtho[2,1-c:1',2'-e]phosphepine 4,5,4',5'-tetrahydro-3H,3'H-4,4'-ethane-1,2-diyl-bis-dinaphtho[2,1-c:1',2'-e]phosphepine 4,5,4',5'-tetrahydro-3H,3'H-4,4'-propane-1,3-diyl-bis-dinaphtho[2,1-c:1',2'-e]phosphepine 4,5,4',5'-tetrahydro-3H,3'H-4,4'-biphen-2,2'-diyl-bis-dinaphtho[2,1-c:1',2'-e]phosphepine 4,5,4',5'-tetrahydro-3H,3'H-4,4'-binaphth-2,2'-diyl-bis-dinaphtho[2,1-c:1',2'-e]phosphepine 4,5,4',5'-tetrahydro-3H,3'H-4,4'-phenylene-1,2-bis-dinaphtho[2,1-c:1',2'-e]phosphepine 4,5,4',5'-tetrahydro-3H,3'H-4,4'-xylylene-1,4-bis-dinaphtho[2,1-c:1',2'-e]phosphepine 4,5,4',5'-tetrahydro-3H,3'H-4,4'-(1,1'-binaphthyl-2,2'-methanediyl)-bis-dinaphtho[2,1-c:1',2'-e]phosphepine 6,7,6',7'-tetrahydro-5H,5'H-6,6'-butane-1,4-diyl-bis-dibenzo[c,e]phosphepine 6,7,6',7'-tetrahydro-5H,5'H-6,6'-methanediyl-bis-dibenzo[c,e]phosphepine 6,7,6',7'-tetrahydro-5H,5'H-6,6'-ethane-1,2-diyl-bis-dibenzo[c,e]phosphepine 6,7,6',7'-tetrahydro-5H,5'H-6,6'-propane-1,3-diyl-bis-dibenzo[c, e]phosphepine 6,7,6',7'-tetrahydro-5H,5'H-6,6'-biphen-2,2'-diyl-bis-dibenzo[c,e]phosphepine 6,7,6',7'-tetrahydro-5H,5'H-6,6'-binaphth-2,2'-diyl-bis-dibenzo[c,e]phosphepine 6,7,6',7'-tetrahydro-5H,5'H-6,6'-phenylene-1,2-diyl-bis-dibenzo[c,e]phosphepine 6,7,6',7'-tetrahydro-5H,5'H-6,6'-xylylene-1,4-diyl-bis-dibenzo[c,e]phosphepine 6,7,6',7'-tetrahydro-5H,5'H-6,6'-(1,1'-binaphthyl-2,2'-methanediyl)-bis-dibenzo[c,e]phosphepine The present invention further relates to two processes for the preparation of the compounds of the formula I.

The first step of both processes is to react a compound of the formula (II), which can be in the (RS), (R) or (S) form and where Ar, $R^1$, $R^2$, $R^3$ and m are defined as indicated above, with a proton-abstracting agent to give a biaryl dianion of the formula (III). In process A, the compound of the formula (III) is then reacted with a compound of the formula (IV), where X is chlorine or bromine and $R^4$ is defined as indicated above, to give (I).

In process B, the dianion (III) is reacted with a phosphorus compound of the formula (V), where X is chlorine or bromine and Z is $NR^5{}_2$ or OAr', $R^5$ being ($C_2$–$C_{16}$)-alkyl and Ar' being a ($C_7$–$C_{20}$)-alkylaryl radical or a phenyl radical which is unsubstituted or substituted by one or more ($C_1$–$C_5$)-alkyl groups, to give the compound (VI). Further reaction of the compound (VI) with the compound (VII), where Y is a leaving group, gives (VIII), from which (I) is obtained by reduction. Leaving groups Y which have proved satisfactory are e.g. halogen, $OSO_2R^6$ and $-N^{\oplus}+R^7{}_3$, $R^6$ being tolyl, $CF_3$, $CH_3$ or F and $R^7$ being ($C_1$–$C_5$)-alkyl or phenyl.

$(R^1)_m-Ar-CHR^2R^3$         (II)
$(R^1)_m-Ar-CHR^2R^3$

↓

$(R^1)_m-Ar-C^{\ominus}R^2R^3$         (III)
$(R^1)_m-Ar-C^{\ominus}R^2R^3$

Process A:

$2\ (III) + X_2P-R^4-PX_2 \rightarrow (I)$         (IV)

Process B:

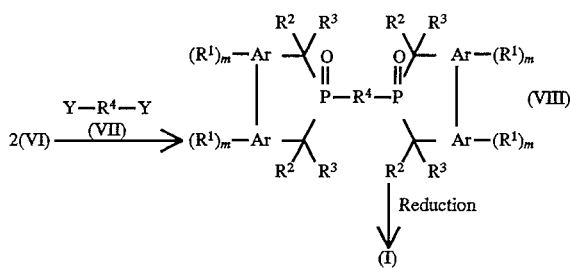

The dianion (III) is prepared by reacting the biaryl compound (II), in the (RS), (R) or (S) form, with at least the stoichiometric amount of a proton-abstracting agent in a polar aprotic or non-polar solvent. The dianion (III), to which a solvent has been added if appropriate, is reacted with the compound (IV) (process A) or (V) (process B). It also possible, however, to take the compound (IV) or (V), to which a solvent has been added if appropriate, and introduce into this solution or suspension the deprotonated compound, to which a solvent has been added if appropriate.

Examples of possible polar aprotic solvents are tetrahydrofuran, diethyl ether or dioxane. Suitable non-polar solvents are aliphatic hydrocarbons.

The proton-abstracting agent used is a strong base such as R'—M, where R' is H, $C_1$- to $C_{10}$-alkyl or amide ($NR''_2$, where R''=H, $C_1$- to $C_{10}$-alkyl) and M is Li, Na, K or Cs. Examples which may be mentioned are sodium hydride, potassium hydride, n-butyllithium, methyllithium, t-butyllithium, sodium amide, lithium tetramethylpiperidide, lithium diisopropylamide and lithium hexamethyldisilazide. n-Butyllithium, t-butyllithium and methyllithium are particularly suitable.

It has proved useful in a number of cases to react the compound (II) and the proton-abstracting agent in a ratio of 1:(2 to 3), especially 1:(2 to 2.2), at −20° to 100° C., especially at 25° to 80° C., if appropriate in the presence of a cation-complexing agent, e.g. N,N,N',N'-tetramethylethylenediamine, N,N,N',N'-tetraethylethylenediamine, 1,5-diazabicyclo[4.3.0]non-5-ene, diazabicyclo[2.2.2]-octane or a crown ether such as 18-crown-6 etc. It is favorable in some cases if the dianion formed is isolated as a complex by filtration and if this complex, to which a solvent or suspending agent has been added if appropriate, is then reacted with the compound (IV) or (V).

The deprotonated compound (III) and the compound (V) are reacted in a ratio of 1:(0.9 to 2), especially 1:(1 to 1.2), at −20° to 100° C., and then worked up with aqueous acid. If a compound (V) in which $Z=NR^5_2$ is used the secondary phosphine oxide (VI) can be separated from the organic phase by crystallization. If a compound (V) in which X=OAr' is used, it can be advantageous if the compound Ar'OH formed by hydrolysis is separated off by distillation and if the secondary phosphine oxide (VI) is then isolated by crystallization.

The secondary phosphine oxide (VI) is then reacted with a base R'—M, where R' and M are as defined above, and the deprotonated compound is then reacted with a compound of the formula (VII) in a ratio of (1.8 to 4):1, especially (2 to 2.4):1, at 0° to 100° C.

The phosphine oxides (VIII) formed are either obtained in high purity and can be used in the subsequent reduction without further purification, or are purified by crystallization.

The phosphine oxide of the formula (VIII), if appropriate in the presence of an inert solvent, is then reduced to the phosphine of the formula (I) by means of a hydride or by means of an organosilane, organodichlorosilane or trichlorosilane. Examples of suitable inert solvents are toluene, o-, m- or p-xylene, mixtures of isomeric xylenes, dioxane or acetonitrile, or mixtures of these solvents.

An example of a possible hydride is lithium aluminum hydride and examples of possible organodichlorosilanes are methyldichlorosilane, ethyldichlorosilane and phenyldichlorosilane.

The phosphine oxide of the formula (VIII) is conventionally reduced at 20° to 170° C., especially 40° to 160° C. and preferably 60° to 150° C.

Whereas process A produces the bis-phosphepines according to the invention in only two reaction steps, process B comprises several stages. However, process B has the advantage that, starting from the central intermediate (VI), a wide variation of $R^4$ is possible by reaction with the compound (VII), which is available in a great variety of structures. The intermediates (IV), on the other hand, are not available in such variety. Rather, some of the latter have to be laboriously synthesized in poor yield (see Zh. Obsch. Khim. 1977, 47, 775; J. Organomet. Chem. 1979, 182, 203; Phosphorus and Sulfur 1983, 15, 155 and Houben-Weyl, Organische Phosphorchemie (Organic Chemistry of Phosphorus) volume E1, 1982, p. 276 et seq.).

The invention also provides compounds of the formulae (VI) and (VIII), wherein $R^1$, $R^2$, $R^3$, $R^4$, Ar and m are as defined above.

The following examples are intended to illustrate the invention without implying a limitation.

EXAMPLE 1

Preparation of 4,5,4',5'-tetrahydro-3H,3'H-4,4'-butane-1,4-diyl-bis-dinaphtho[2,1-c:1',2'-e] phosphepine (Process B)

a) 4,5-Dihydro-3H-dinaphtho[2,1-c:1',2'-e]phosphepine-4-oxide

In the absence of air and moisture, 27.8 g (99 mmol) of 2,2'-dimethyl-1,1'-binaphthyl are added in portions to 30.5 g (202 mmol) of tetramethylethylenediamine and 125 ml (200 mmol) of a 1.6M solution of n-butyllithium in hexane. The mixture is stirred for 2 h at 65° C. and cooled to 20° C. and the solid is filtered off on an inverted frit and washed with heptane. After drying under high vacuum, 25.5 g (49 mmol) of a dianion are obtained as deep red crystals. Under argon, these crystals are added in portions to a solution of 15.1 g (49 mmol) of phosphorous acid 2,4-di-tert-butylphenyl ester dichloride in 50 ml of heptane, the reaction mixture warming up to 60° C. It is stirred for 1 h at 25° to 60° C. and left to stand for 16 hours at 25° C. 50 ml of water and 50 ml of 1M sulfuric acid are added dropwise, the phases are separated and the organic phase is dried over magnesium sulfate and concentrated to give 28.6 g of a yellow oil. The 2,4-di-tert-butylphenol formed is distilled off under high vacuum and the residue is crystallized from toluene/heptane=5/1 to give 5.6 g of pale yellow crystals melting at 242° to 246° C.

$^{31}$P NMR: δ (CDCl$_3$)=44.2 ppm b) 4,5,4',5'-Tetrahydro-3H,3'H-4,4'-butane-1,4-diyl-bis-dinaphtho[2,1-c:1',2'-e]phosphepine 4,4'-dioxide 17.2 ml (27.5 mmol) of a 1.6M solution of n-butyllithium in hexane are added dropwise at 0° C. to a solution of 8.19 g (25 mmol) of 4,5-dihydro-3H-dinaphtho[2,1-c:1',2'-e] phosphepine 4-oxide (Example 1a) in 50 ml of dry THF. The solution is then stirred for 1 h at 0° C. and 3 h at 25° C. 2.69 g (12.5 mmol) of 1,4-dibromobutane are then added dropwise and the mixture is stirred for 6 h at 25° C. The solvent is distilled off under vacuum and the residue is extracted with dichloromethane/water. The organic phase is separated off, dried over sodium sulfate and concentrated to give 8.17 g (92%) of colorless crystals. Column chromatography with silica gel and ethyl acetate as eluent gave 5.29 g (60%) of colorless crystals.

$^{31}$P NMR (CDCl$_3$): δ=65.33 ppm C$_{48}$H$_{40}$O$_2$P$_2$ (720.726) Calc.: C 81.1 H 5.7 P 8.7 O 4.5 Found: C 81.0 H 5.7 P 8.6 c) 4,5,4',5'-Tetrahydro-3H,3'H-4,4'-butane-1,4-diyl-bis-dinaphtho[2,1-c:1',2'-e]phosphepine 3.55 g (5 mmol) of 4,5,4',5'-tetrahydro-3H,3'H-4,4'-butane-1,4-diyl-bis-dinaphtho[2,1-c:1',2'-e]phosphepine 4,4'-dioxide, 5.16 ml (22 mmol) of tributylamine and 2.29 g (20 mmol) of methyldichlorosilane are refluxed for 15 h in 120 ml of o-xylene. The o-xylene is distilled off at normal pressure and the residue is left to cool to RT. The colorless crystals which form are filtered off with suction under argon and washed with acetone to give 2.88 g (85%) of colorless crystals.

$^{31}$P NMR (CDCl$_3$): δ=6.57 ppm

EXAMPLE 2

Preparation of 4,5,4',5'-tetrahydro-3H,3'H-4,4'-butane-1,4-diyl-bis-dinaphtho[2,1-c:1',2'-e]phosphepine (Process A)

20.8 g (0.04 mol) of the dianion of 2,2'-dimethyl-1,1'-binaphthyl as the bis-tetramethylethylenediamine complex, prepared as in Example 1a), are added in portions at 0° C. to a solution of 5.2 g (0.02 mol) of 1,4-bis(dichlorophosphino)butane (Phosphorus and Sulfur 1983, 15, 155) in 30 ml of dry heptane. The mixture is then heated to 30° C. and stirred for 10 hours. It is digested with 50 ml of water and the precipitate formed is filtered off and washed with degassed heptane. It is dried under vacuum and crystallized from degassed toluene to give 4.7 g (35%) of colorless crystals.

$^{31}$P NMR (CDCl$_3$): δ=6.57 ppm

EXAMPLE 3

Preparation of 4,5,4',5'-tetrahydro-3H,3'H-methanediyl-bis-dinaphtho[2,1-c:1',2'-e]phosphepine (Process B)

a) See Example 1a)

b) 4,5,4',5'-Tetrahydro-3H,3'H-methanediyl-bis-dinaphtho[2,1-c1',2'-e]phosphepine 4,4'-dioxide 17.2 ml (27.5mmol) of a 1.6M solution of n-butyllithium in hexane are added dropwise at 0° C. to a solution of 8.19 g (25mmol) of 4,5-dihydro-3H-dinaphtho[2,1-c:1',2'-e]phosphepine 4-oxide (Example 1a) in 50 ml of dry THF. The solution is then stirred for 1 h at 0° C. and 3 h at 25° C. 1.06 g (12.5 mmol) of dichloromethane are then added dropwise at 0° C. and the mixture is stirred for 6 h at 25° C. The solvent is distilled off under vacuum and the residue is extracted with dichloromethane/water. The organic phase is separated off, dried over sodium sulfate and concentrated to give 7.6 g (91%) of a colorless oil. Column chromatography with silica gel and ethyl acetate gave 4.6 g (55%) of colorless crystals.

$^{31}$P NMR (CDCl$_3$): δ=60.38 and 60.23 ppm MS (EI): M$^1$=668 c) 4,5,4',5'-Tetrahydro-3H,3'H-methanediyl-bis-dinaphtho[2,1-c:1',2'-e]phosphepine 3.34 g (5 mmol) of 4,5,4',5'-tetrahydro-3H,3'H-methanediyl-bis-dinaphtho[2,1-c:1',2'-e]phosphepine 4,4'-dioxide, 5.16 ml (22 mmol) of tributylamine and 2.29 g (20 mmol) of methyldichlorosilane are refluxed for 15 h in 120 ml of o-xylene. The o-xylene is distilled off at normal pressure and the residue is left to cool to 20° C. 5 ml of degassed acetone are added and the colorless crystals which form are filtered off with suction and washed with acetone to give 1.85 g (58%) of colorless crystals.

$^{31}$P NMR (CDCl$_3$): δ=−0.7 and −1.0 ppm

I claim:

1. A bis-phosphepine of the formula (I):

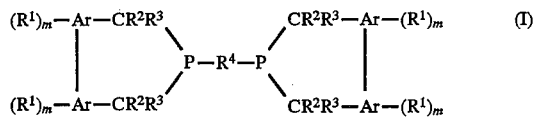

where:

Ar—Ar is biphenyl, 1,1'-binaphthyl or 1-phenylnaphthyl,

R$^1$ independently of one another are F, (C$_1$–C$_8$)-alkyl or (C$_1$–C$_8$)-alkoxy, m is 0, 1, 2, 3 or 4, R$^2$ and R$^3$ independently of one another are H, (C$_1$–C$_{20}$)-alkyl, (C$_6$–C$_{20}$)-aryl, (C$_7$–C$_{20}$)-aralkyl, (C$_7$–C$_{20}$)-alkaryl or (C$_3$–C$_{20}$)-cycloalkyl and R$^4$ is (C$_1$–C$_{10}$)-alkylene, it also being possible for the alkylene chain to contain oxygen atoms and N-alkyl groups, (C$_3$–C$_{10}$)-cycloalkylene, (C$_8$–C$_{22}$)-arylenebisalkyl or (C$_6$–C$_{10}$)-arylene, the group CR2R$^3$ always being adjacent to the Ar—Ar bond.

2. A compound as claimed in claim 1 which has (R,S), (R,R), (S,S) or (RS) stereochemistry.

3. A compound as claimed in claim 1, wherein R$^4$ is methylene, ethylene, n-propylene, n-butylene, phenylene, xylylene, biphenylene or naphthylene.

4. A compound as claimed in claim 1, wherein m is equal to zero and R$^2$ and R$^3$ are hydrogen.

5. A compound as claimed in claim 1, wherein the compound of formula I is a compound of the formula (VIII)

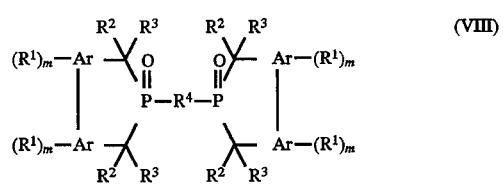

where R$^1$, R$^2$, R$^3$, R$^4$, Ar and m are as defined in claim 1.

6. 4,5,4',5'-Tetrahydro-3H,3'H-4,4'-butane-1,4-diyl-bis-dinaphtho(2,1-c:1',2'-e)phosphepine 4,5,4',5'-tetrahydro-3H, 3'H-4,4'-methanediyl-bis-dinaphtho(2,1-c:1',2'-e) phosphepine, 4,5,4',5'-tetrahydro-3H,3'H-4,4'-ethane-1,2-diyl-bis-dinaphtho(2,1-c:1',2'-e)phosphepine, 4,5,4',5'-tetrahydro-3H,3'H-4,4'-propane-1,3-diyl-bis-dinaphtho(2,1-c:1',2'-e)phosphepine, 4,5,4',5'-tetrahydro-3H,3'H-4,4'-biphen-2,2'-diyl-bis-dinaphtho(2,1-c:1',2'-e)phosphepine, 4,5,4',5'-tetrahydro-3H,3'H-4,4'-binaphth-2,2'-diyl-bis-dinaphtho(2,1-c:1',2'-e)phosphepine, 4,5,4',5'-tetrahydro-3H,3'H-4,4'-phenylene-1,2-bis-dinaphtho(2,1-c:1',2'-e)phosphepine, 4,5,4',5'-tetrahydro-3H,3'H-4,4'-xylylene-1,4-bis-dinaphtho(2,1-c:1',2'-e)phosphepine, 4,5,4',5'-tetrahydro-3H,3'H-4,4'-(1,1'-binaphthyl-2,2'-methanediyl)-bis-dinaphtho(2,1-c:1',2'-e)phosphepine, 6,7,6',7'-tetrahydro-5H,5'H-6,6'-butane-1,4-diyl-bis-dibenzo(c,e) phosphepine, 6,7,6',7'-tetrahydro-5H,5'H-6,6'-methanediyl-bis-dibenzo(c,e)phosphepine, 6,7,6',7'-tetrahydro-5H,5'H-6, 6'-ethane-1,2-diyl-bis-dibenzo(c,e)phosphepine, 6,7,6',7'-tetrahydro-5H,5'H-6,6'-propane-1,3-diyl-bis-dibenzo(c,e)phosphepine, 6,7,6',7'-tetrahydro-5H,5'H-6,6'-biphen-2,2'-diyl-bis-dibenzo(c,e)phosphepine, 6,7,6',7'-tetrahydro-5H,5'H-6,6'-binaphth-2,2'-diyl-bis-dibenzo(c,e)phosphepine, 6,7,6',7'-tetrahydro-5H,5'H-6,6'-phenylene-1,2-diyl-bis-dibenzo(c,e)phosphepine, 6,7,6',7'-tetrahydro-5H,5'H-6,6'-xylylene-1,4-diyl-bis-dibenzo(c,e)phosphepine or 6,7,6',7'-tetrahydro-5H,5'H-6,6'-(1,1'-binaphthyl-2,2'-methanediyl)-bis-dibenzo(c,e)phosphepine.

* * * * *